United States Patent [19]

Yazawa et al.

[11] Patent Number: 5,246,841
[45] Date of Patent: Sep. 21, 1993

[54] MICROBIAL PROCESS FOR PRODUCTION OF EICOSAPENTAENOIC ACID

[75] Inventors: Kazunaga Yazawa, Sagamihara; Keiko Araki, Machida, both of Japan; Noriko Okazaki, Rockville, Md.; Naganori Numao, Sagamihara; Kiyosi Kondo, Yamato, both of Japan

[73] Assignee: Sagami Chemical Research Center, Tokyo, Japan

[21] Appl. No.: 781,659

[22] Filed: Oct. 25, 1991

Related U.S. Application Data

[63] Continuation of Ser. No. 136,129, Dec. 21, 1987, abandoned.

[30] Foreign Application Priority Data

| | | |
|---|---|---|
| Dec. 26, 1986 [JP] | Japan | 61-308784 |
| Feb. 2, 1987 [JP] | Japan | 62-20510 |
| Feb. 2, 1987 [JP] | Japan | 62-20511 |
| Mar. 6, 1987 [JP] | Japan | 62-49932 |
| Apr. 2, 1987 [JP] | Japan | 62-79806 |

[51] Int. Cl.$^5$ ............................ C12P 7/64; C12N 1/20
[52] U.S. Cl. .................................. 435/134; 435/252.1; 435/874; 435/872; 435/253.3
[58] Field of Search ............ 435/134, 874, 822, 252.1, 435/253.3

[56] References Cited

FOREIGN PATENT DOCUMENTS 62-56497 3/1987 Japan .................................... 435/134

OTHER PUBLICATIONS

MacDonnell et al, *Syst. and Appl. Microbiol.* vol. 6, pp. 171–182 (1985).

Wilkinson et al., *J of Gen Microbiol.* 1980, vol. 118, pp. 329–341.
J. Gellerman et al, Biochimica et Biophysica Acta, 573 (1979) 23–30.
Carl O. Wirsen et al, Current Microbiology vol. 14 (1987), 319–322.
Program of Conference (1986) of Fermentation Technology Association of Japan. (Abstract only).
Summary of Meeting (1987) of Agricultural Chemistry Association of Japan. (Abstract Only).
Chemical Abstracts, vol. 104, No. 23, Jun. 9, 1986, pp. 603, Abstract No. 205535r.
Chemical Abstracts, vol. 105, No. 25, Dec. 22, 1986, pp. 625, Abstract No. 224604y.
Chemical Abstracts, vol. 107, No. 1, Jul. 6, 1987, pp. 363, Abstract No. 39111m.

*Primary Examiner*—Irene Marx
*Attorney, Agent, or Firm*—Nixon & Vanderhye

[57] ABSTRACT

A process for the production of eicosapentaenoic acid comprising the steps of a) culturing a microorganism capable of producing lipid containing eicosapentaenoic acid belonging to a genus selected from the group of Pseudomonas, Alteromonas and Shewanella, to produce lipid containing eicosapentaenoic acid, and b) recovering the eicosapentaenoic acid from the cultured product; a process for production of a lipid containing eicosapentaenoic acid comprising the steps of a) culturing a microorganism capable of producing lipid containing eicosapentaenoic acid belonging to a genus selected from the group of Pseudomonas, Alteromonas and Shewanella, to produce lipid containing eicosapentaenoic acid, and b) recovering the lipid containing eicosapentaenoic acid; and microorganisms capable of producing eicosapentaenoic acid belonging to a genus selected from the group consisting of Pseudomonas, Alteromonas, and Shewanella.

7 Claims, No Drawings

MICROBIAL PROCESS FOR PRODUCTION OF EICOSAPENTAENOIC ACID

This is a continuation of application Ser. No. 07/136,129, filed Dec. 21, 1987 now abandoned.

BACKGROUND OF THE INVENTION

1. Field of the Invention

The present invention relates to novel processes for the production of eicosapentaenoic acid and lipid containing eicosapentaenoic acid, by fermentation and using microorganisms belonging to the genus Pseudomonas, Alteromonas or Shewanella.

2. Description of the Related Art

Poly-unsaturated fatty acids represented by eicosapentaenoic acid are important as a component of biomembranes in an organism. The known pharmacological actions of eicosapentaenoic acid include blood platelet coagulation-inhibition (thrombolytic action), lowering of blood level of neutral fat, lowering of blood levels of VLDL-cholesterol and LDL-cholesterol and increase of blood level of HDL-cholesterol (anti-atherosclerotic action), lowering of blood viscosity, anti-hypertension, anti-inflammation, and anti-tumor actions. Moreover, eicosapentaenoic acid acts as a substrate for the formation of the group of prostaglandins, and thus are essential for higher mammals including humans. In particular, eicosapentaenoic acid is, important as a substrate for the type 3 prostaglandin, inhibits a blood platelet coagulation action, and is promising as a therapeutic and propylactic agent for thrombosis. Moreover, among poly-unsaturated fatty acids responsible for lowering the plasma cholesterol level, eicosapentaenoic acid in particular exhibits a high level of activity in lowering the plasma cholesterol level. Therefore, eicosapentaenoic acid is extremely effective in comparison with other fatty acids, such as linoleic acid, naturally present in plant oil. Eicosapentaenoic acid is also known to be an essential nutrient for fish.

An epidemiological study disclosed by Dyerberg, Am. J. Clin. Nutr. 28, 958, 1975, Denmark suggests the probability of using eicosapentaenoic acid as a pharmaceutical agent and diet food on the basis of the anti-thrombotic action and lipid-lowering action thereof. However, as evident from the structure thereof, a chemical synthesis of eicosapentaenoic acid is very difficult, and therefore, the industrial production of eicosapentaenoic acid is difficult. Under these circumstances, an ingestion of sardine, mackerel, and saury containing a relatively large amount of eicosapentaenoic acid is recommended.

At present, the commercial eicosapentaenoic acid-containing products provided for diet foods are obtained from fish oil prepared by cooking fish, and contain eicosapentaenoic acid in an amount of 10 to 30% by weight. Fish oil prepared by the cooking process comprises a mixture of glycerides which contain various kinds of fatty acids, and therefore, the isolation of eicosapentaenoic acid from the fish oil is difficult. Moreover, since eicosapentaenoic acid is a straight-chain fatty acid with 20 carbon atoms containing five double bonds, all of which are in a cis configuration, it is unstable and susceptible to oxidation. Therefore, the isolation of eicosapentaenoic acid from fish oil must be carried out in such a manner that oxygen, light, and heat are excluded during the process. Moreover, it is difficult to eliminate organic solvents used for the isolation of eicosapentaenoic acid from the product under the usual reduced pressure. Therefore, a complete elimination of the organic solvents is a problem from the technical and economical points of view.

The eicosapentaenoic acid used for pharmaceutical purposes is produced by hydrolysing fish oil extracted by any method, with enzymes, or under an alkaline conditions, to liberate free fatty acids, and optionally, converting the fatty acids to methyl esters or ethyl esters thereof, subjecting the esters to fractional crystallization under a low temperature, urea-addition, distillation under a reduced pressure, reverse phase chromatography or the like, to prepare a product containing at least 90% eicosapentaenoic acid. However, the eicosapentaenoic acid concentrates thus prepared contain organic residual solvents used in the extraction process and have been deteriorated by intermolecular polymerization, isomerization, oxidation or the like. Moreover, eicosapentaenoic acid products produced from fish oil might contain docosenoic acids, which are suspected to be a causal substance of cardio disease, and therefore it is a problem to use them in diet food and pharmaceuticals. Finally, eicosapentaenoic acid products produced from fish oil may emit an unpleasant "fishy" odor.

Recently, to eliminate the above-mentioned disadvantages originating from the use of fish, processes for the production of eicosapentaenoic acid using microorganisms such as chlorella, phaeodactylum, euglena, or algae have been disclosed. For example, J. L. Gellerman and H. Schlenk, BBA, 573, 23, 1979, and Yamada et al, at the Conference of the Fermentation Technology Association of Japan, 1986, reported fungi which produce eicosapentaenoic acid. Such microbial processes for the production of eicosapentaenoic acid are advantageous in that isolation and purification of the target fatty acid from a microbially produced fatty acid mixture is relatively easy, and a preferential production of the target fatty acid in relation to other fatty acids is relatively simple if the fermentation process can be controlled. However, the above mentioned processes require a incubation time of as long as seven days to one month.

Moreover, Summary of the Conference of the Association of Agricultural Chemistry of Japan published on Mar. 10, 1987 discloses production of arachidonic acid and eicosapentaenoic acid by Mortierella.

SUMMARY OF THE INVENTION

Accordingly the present invention provides a novel process for the production of eicosapentaenoic acid by a fermentation process using bacteria which grows very rapidly in comparison with the above-mentioned prior art organisms, which process provides low production cost and a high level of purity of the target eicosapentaenoic acid.

More specifically, the present invention provides a process for the production of eicosapentaenoic acid comprising the steps of:

a) culturing a microorganism capable of producing lipid containing eicosapentaenoic acid belonging to a genus selected from the group of Pseudomonas, Alteromonas and Shewanella to produce lipid containing eicosapentaenoic acid; and b) recovering the eicosapentaenoic acid from the culture.

Moreover, the present invention provides a process for the production of a lipid containing eicosapentaenoic acid comprising the steps of:

a) culturing the above-mentioned microorganism to produce eicosapentaenoic acid as a component of lipids; and b) recovering the lipid containing eicosapentaenoic acid from the culture.

Moreover, the present invention provides novel microorganisms capable of producing lipid containing eicosapentaenoic acid belonging the above-mentioned genera.

DESCRIPTION OF THE PREFERRED EMBODIMENT

According to the present invention, any microorganisms capable of producing eicosapentaenoic acid and belonging to a genus selected from the group consisting of *Pseudomonas*, *Alteromonas*, and *Shewanella*, can be used.

Examples of strains belonging to *Pseudomonas* according to the present invention include *Pseudomonas putrefaciens* SCRC-2181, SCRC-2201, SCRC-2271, SCRC-2341, SCRC-2451, SCRC-2642, SCRC-2792, SCRC-2878, SCRC-3011 and SCRC-3022, which have been newly isolated and identified by the present inventors.

Examples of strains belonging to *Alteromonas* are *Alteromonas putrefaciens*, such as *Alteromonas putrefaciens* SCRC-2871 and *Alteromonas putrefaciens* subspecies *sagamifaciens* SCRC-1162, which have been newly isolated and identified by the present inventors. Moreover, known strains of *Alteromonas putrefaciens* IAM-1510, and IAM-12425 are available from the Institute of Applied Microbiology, University of Tokyo, Yayoi 1-1-1, Bunkyo-ku, Tokyo, Japan 113 (IAM), and can be used for the production of eicosapentaenoic acid. Further, microorganisms belonging to Alteromonas are *Alteromonas hanedai*, such as *Alteromonas hanedai* IAM-12641, which is also available from the IAM.

A microorganism capable of producing eicosapentaenoic acid and belonging to *Shewanella* is, for example, *Shewanella putrefaciens* SCRC-2874, which has been newly isolated and identified by the present inventor.

The above-mentioned new strains were isolated according to the following procedure. Namely, the plate medium of a composition set forth in, Table 1 was prepared.

TABLE 1

| Meat extract | 1% |
| Peptone | 1% |
| NaCl | 0.5% |
| Agar | 1.5% |
| Water | |
| | (pH 7.0) |

To this agar medium, a sample obtained from various marine sources, which had been appropriately diluted with physiological saline, was inoculated, and the agar plate was incubated at 25° C. for one or two days to develop microbial colonies. The colonies were picked up to slant media having the same composition as described above. In this manner, many strains were isolated from samples obtained from various marine areas.

A medium with the same composition as described above, except that the agar was omitted, was distributed to test tubes in an amount of 5 ml per tube, and autoclaved. The strains isolated as described above were inoculated to the test tubes, which were then incubated at 25° C. for one or two days. The cultures were then assayed to determine the content of eicosapentaenoic acid. The origins of the isolated strains are shown in Table 2.

TABLE 2

| Strains | Origin |
| --- | --- |
| SCRC-2181, SCRC-2201, SCRC-2271 | Tokyo Bay |
| SCRC-2341, SCRC-2451, SCRC-2642, SCRC-2792, SCRC-2871, SCRC-2874, SCRC-1162, SCRC-2878 | Sagami Bay |
| SCRC-3011, SCRC-3022 | Sanriku Beach |

The taxonomical properties of the above-mentioned strains are shown in Table 3.

TABLE 3

| Observation | | SCRC-2181 | SCRC-2201 | SCRC-2271 | SCRC-2341 | SCRC-2451 |
| --- | --- | --- | --- | --- | --- | --- |
| a) | Morphology | | | | | |
| | 1 Shape of cell | short rod | short rod | short rod | short rod | short rod |
| | Size | 1.0 × 2.0 µm | 1.0 × 2.0 µm | 1.0 × 2.0 µm | 1.0 × 2.0 µm | 1.0 × 2.0 µm |
| | 2 Pleomorphism | none | none | none | none | none |
| | 3 Motility | + | + | + | + | + |
| | Flagella | single polar | single polar | single polar | single polar | single polar |
| | 4 Sporulation | − | − | − | − | − |
| | 5 Gram stain | − | − | − | − | − |
| | 6 Acid-fastness | − | − | − | − | − |
| b) | Growth characteristics | | | | | |
| | 1 Bouillon agar plate (at 29° C., for 2 days) | | | | | |
| | Size of colony | 2.0–2.4 mm | 2.0–2.4 mm | 2.0–2.4 mm | 2.0–2.4 mm | 2.0–2.4 mm |
| | Shape of colony | round | round | round | round | round |
| | Surface of colony | smooth | smooth | smooth | smooth | smooth |
| | Elevation of colony | raised | raised | raised | raised | raised |
| | Edge of colony | entire | entire | entire | entire | entire |
| | Color of colony | light yellow | light yellow | light yellow | light yellow | light yellow |
| | Transparency of colony | opaque | opaque | opaque | opaque | opaque |
| | Gloss of colony | dull | dull | dull | dull | dull |
| | Formation of soluble pigment | − | − | − | − | − |
| | 2 Bouillon agar slant (at 25° C., for 2 days) | | | | | |
| | Growth | abundant | abundant | abundant | abundant | abundant |
| | Gloss of colony | dull | dull | dull | dull | dull |
| | 3 Bouillon liquid (at 25° C., for 2 days) | | | | | |
| | Growth at surface | none | none | none | none | none |
| | Turbidity | turbid | turbid | turbid | turbid | turbid |
| | Precipitation | powdery | powdery | powdery | powdery | powdery |
| | Gas formation | none | none | none | none | none |

TABLE 3-continued

| | | | | | | |
|---|---|---|---|---|---|---|
| | 4 Bouillon gelatin (at 25° C., for 2 days) | | | | | |
| | Gelatin liquefaction | liquefied | liquefied | liquefied | liquefied | liquefied |
| | Litmus milk | no coagulation change to yellow | no coagulation change to yellow | no coagulation change to yellow | no coagulation change to yellow | no coagulation change to yellow |
| c) | Physiological properties | | | | | |
| | 1 Nitrate reduction | + | + | + | + | + |
| | 2 Denitrification | − | − | − | − | − |
| | 3 Methylred test | − | − | − | − | − |
| | 4 Voges-Proskauer test | − | − | − | − | − |
| | 5 Indole production | − | − | − | − | − |
| | 6 Hydrogen sulfide formation | + | + | + | + | + |
| | 7 Hydrolysis of Starch | − | − | − | − | − |
| | 8 Citrate utilization | | | | | |
| | Koser | + | + | + | + | + |
| | Christensen | + | + | + | + | + |
| | 9 Nitrate utilization | + | + | + | + | + |
| | 10 Pigment formation | | | | | |
| | King A medium | − | − | − | − | − |
| | King B medium | − | − | − | − | − |
| | 11 Urease | − | − | − | − | − |
| | 12 Oxidase | + | + | + | + | + |
| | 13 Catalase | + | + | + | + | + |
| | 14 Growth range | | | | | |
| | pH | 6–9 | 6–9 | 6–9 | 6–9 | 6–9 |
| | Temperature | 5–30° C. | 5–30° C. | 5–30° C. | 5–30° C. | 5–30° C. |
| | 15 Oxygen requirement | aerobic | aerobic | aerobic | aerobic | aerobic |
| | 16 O—F test (glucose) | − | − | − | − | − |
| | 17 Acid/gas formation from sugar | | | | | |
| | 1. L-Arabinose | − | + | + | + | + |
| | 2. D-Xylose | − | − | − | − | − |
| | 3. D-Glucose | + | + | + | + | + |
| | 4. D-Mannose | − | − | − | − | − |
| | 5. D-Fructose | + | + | + | + | + |
| | 6. D-Galactose | − | − | − | + | − |
| | 7. Maltose | + | + | + | + | + |
| | 8. Sucrose | + | + | + | + | + |
| | 9. Lactose | − | − | − | − | − |
| | 10. Trehalose | − | − | − | − | − |
| | 11. D-Sorbitol | − | − | − | − | − |
| | 12. D-Mannitol | − | − | − | − | − |
| | 13. Inositol | − | − | − | − | − |
| | 14. Glycerol | − | − | − | − | − |
| | 15. Starch | − | − | − | − | − |
| | (No gas production in each case) | | | | | |
| d) | Other properties | | | | | |
| | Growth on SS agar medium | + | + | + | + | + |
| | Growth on MacConkey agar medium | + | + | + | + | + |
| | Growth on 6.5% NaCl | + | + | + | + | + |
| | DNase | + | + | + | + | + |
| | Ornithine decarboxylase | + | + | + | + | + |
| | Arginine dehydrolation | − | − | − | − | − |
| | Gelatin liquefaction | + | + | + | + | + |
| Observation | | SCRC-2642 | SCRC-2792 | SCRC-2878 | SCRC-3011 | SCRC-3022 |
| a) | Morphology | | | | | |
| | 1 Shape of cell | short rod | short rod | short rod | short rod | short rod |
| | Size | 1.0 × 2.0 μm | 1.0 × 2.0 μm | 1.0 × 2.0 μm | 1.0 × 2.0 μm | 1.0 × 2.0 μm |
| | 2 Pleomorphism | none | none | none | none | none |
| | 3 Motility | + | + | + | + | + |
| | Flagella | single polar | single polar | single polar | single polar | single polar |
| | 4 Sporulation | − | − | − | − | − |
| | 5 Gram stain | − | − | − | − | − |
| | 6 Acid-fastness | − | − | − | − | − |
| b) | Growth characteristics | | | | | |
| | 1 Bouillon agar plate (at 25° C., for 2 days) | | | | | |
| | Size of colony | 2.0–2.4 mm | 2.0–2.4 mm | 2.0–2.4 mm | 2.0–2.4 mm | 2.0–2.4 mm |
| | Shape of colony | round | round | round | round | round |
| | Surface of colony | smooth | smooth | smooth | smooth | smooth |
| | Elevation of colony | raised | raised | raised | raised | raised |
| | Edge of colony | entire | entire | entire | entire | entire |
| | Color of colony | light yellow | light yellow | light yellow | light yellow | light yellow |
| | Transparency of colony | opaque | opaque | opaque | opaque | opaque |
| | Gloss of colony | dull | dull | dull | dull | dull |
| | Formation of soluble pigment | − | − | − | − | − |
| | 2 Bouillon agar slant (at 25° C., for 2 days) | | | | | |
| | Growth | abundant | abundant | abundant | abundant | abundant |
| | Gloss of colony | dull | dull | dull | dull | dull |
| | 3 Bouillon liquid (at 25° C., for 2 days) | | | | | |
| | Growth at surface | none | none | none | none | none |

TABLE 3-continued

| | | | | | | |
|---|---|---|---|---|---|---|
| | Turbidity | turbid | turbid | turbid | turbid | turbid |
| | Precipitation | powdery | powdery | powdery | powdery | powdery |
| | Gas formation | none | none | none | none | none |
| 4 | Bouillon gelatin (at 25° C., for 2 days) | | | | | |
| | Gelatin liquefaction | liquefied | liquefied | liquefied | liquefied | liquefied |
| | Litmus milk | no coagulation change to yellow | no coagulation change to yellow | no coagulation change to yellow | no coagulation change to yellow | no coagulation change to yellow |
| c) | Physiological properties | | | | | |
| 1 | Nitrate reduction | + | + | + | + | + |
| 2 | Denitrification | − | − | − | − | − |
| 3 | Methylred test | − | − | − | − | − |
| 4 | Voges-Proskauer test | − | − | − | − | − |
| 5 | Indole production | − | − | − | − | − |
| 6 | Hydrogen sulfide formation | + | + | + | + | + |
| 7 | Hydrolysis of starch | − | − | − | − | − |
| 8 | Citrate utilization | | | | | |
| | Koser | + | + | + | + | + |
| | Christensen | + | + | + | + | + |
| 9 | Nitrate utilization | + | + | + | + | + |
| 10 | Pigment formation | | | | | |
| | King A medium | − | − | − | − | − |
| | King B medium | − | − | − | − | − |
| 11 | Urease | − | − | − | − | − |
| 12 | Oxidase | + | + | + | + | + |
| 13 | Catalase | + | + | + | + | + |
| 14 | Growth range | | | | | |
| | pH | 6-9 | 6-9 | 6-9 | 6-9 | 6-9 |
| | Temperature | 5-30° C. | 5-30° C. | 5-30° C. | 5-30° C. | 5-30° C. |
| 15 | Oxygen requirement | aerobic | aerobic | aerobic | aerobic | aerobic |
| 16 | O—F test (glucose) | − | − | − | − | − |
| 17 | Acid/gas formation from sugar | | | | | |
| | 1. L-Arabinose | − | − | − | − | − |
| | 2. D-Xylose | − | − | − | − | − |
| | 3. D-Glucose | + | + | + | + | + |
| | 4. D-Mannose | − | − | − | − | − |
| | 5. D-Fructose | + | + | + | + | + |
| | 6. D-Galactose | + | − | − | + | + |
| | 7. Maltose | + | + | + | + | + |
| | 8. Sucrose | + | + | + | + | + |
| | 9. Lactose | − | − | − | − | − |
| | 10. Trehalose | − | − | − | − | − |
| | 11. D-Sorbitol | − | − | − | − | − |
| | 12. D-Mannitol | − | − | − | − | − |
| | 13. Inositol | − | − | − | − | + |
| | 14. Glycerol | − | − | − | − | − |
| | 15. Starch | − | − | − | − | − |
| | (No gas production in each case) | | | | | |
| d) | Other properties | | | | | |
| | Growth on SS agar medium | + | + | + | + | + |
| | Growth on MacConkey agar medium | + | + | + | + | + |
| | Growth on 6.5% NaCl | + | + | + | + | + |
| | DNase | + | + | + | + | + |
| | Ornithine decarboxylase | + | + | + | + | + |
| | Arginine dehydrolation | − | − | − | − | − |
| | Gelatin liquefaction | + | + | + | + | + |

| Observation | | SCRC-2871 | SCRC-2874 | SCRC-1162 |
|---|---|---|---|---|
| a) | Morphology | | | |
| 1 | Shape of cell | short rod | short rod | short rod |
| | Size | 1.0 × 2.0 μm | 1.0 × 2.0 μm | 1.0 × 2.0 μm |
| 2 | Pleomorphism | none | none | none |
| 3 | Motility | + | + | + |
| | Flagella | single polar | single polar | peritrichous |
| 4 | Sporulation | − | − | − |
| 5 | Gram stain | − | − | − |
| 6 | Acid-fastness | − | − | − |
| b) | Growth characteristics | | | |
| 1 | Bouillon agar plate (at 25° C., for 2 days) | | | |
| | Size of colony | 2.0-2.4 mm | 2.0 × 2.4 mm | 0.6-0.8 mm |
| | Shape of colony | round | round | round |
| | Surface of colony | smooth | smooth | smooth |
| | Elevation of colony | raised | raised | raised |
| | Edge of colony | entire | entire | entire |
| | Color of colony | light yellow | light yellow | light yellow |
| | Transparency of colony | opaque | opaque | translucent |
| | Gloss of colony | dull | dull | dull |
| | Formation of soluble pigment | − | − | − |
| 2 | Bouillon agar slant (at 25° C., for 2 days) | | | |
| | Growth | abundant | abundant | abundant |

TABLE 3-continued

|   |   |   |   |   |
|---|---|---|---|---|
|   | Gloss of colony | dull | dull | dull |
| 3 | Bouillon liquid (at 25° C., for 2 days) | | | |
|   | Growth at surface | none | none | none |
|   | Turbidity | turbid | turbid | turbid |
|   | Precipitation | powdery | powdery | powdery |
|   | Gas formation | none | none | none |
| 4 | Bouillon gelatin (at 25° C., for 2 days) | | | |
|   | Gelatin liquefaction | liquefied | liquefied | liquefied |
|   | Litmus milk | no coagulation change to yellow | no coagulation change to yellow | no change |
| c) | Physiological properties | | | |
| 1 | Nitrate reduction | + | + | + |
| 2 | Denitrification | − | − | − |
| 3 | Methylred test | − | − | − |
| 4 | Voges-Proskauer test | − | − | − |
| 5 | Indole production | − | − | − |
| 6 | Hydrogen sulfide formation | + | + | + |
| 7 | Hydrolysis of starch | − | − | − |
| 8 | Citrate utilization | | | |
|   | Koser | + | + | − |
|   | Christensen | + | + | − |
| 9 | Nitrate utilization | + | + | − |
| 10 | Pigment formation | | | |
|   | King A medium | − | − | − |
|   | King B medium | − | − | − |
| 11 | Urease | − | − | + |
| 12 | Oxidase | + | + | + |
| 13 | Catalase | + | + | + |
| 14 | Growth range | | | |
|   | pH | 6-9 | 6-9 | 6-9 |
|   | Temperature | 5-30° C. | 5-30° C. | 5-30° C. |
| 15 | Oxygen requirement | aerobic | aerobic | aerobic |
| 16 | O—F test (glucose) | − | − | − |
| 17 | Acid/gas formation from sugar | | | |
|   | 1. L-Arabinose | − | − | − |
|   | 2. D-Xylose | − | − | − |
|   | 3. D-Glucose | + | + | + |
|   | 4. D-Mannose | − | − | − |
|   | 5. D-Fructose | + | + | + |
|   | 6. D-Galactose | − | − | − |
|   | 7. Maltose | + | + | − |
|   | 8. Sucrose | + | + | − |
|   | 9. Lactose | − | − | − |
|   | 10. Trehalose | − | − | − |
|   | 11. D-Sorbitol | − | − | − |
|   | 12. D-Mannitol | − | − | − |
|   | 13. Inositol | − | − | − |
|   | 14. Glycerin | − | − | − |
|   | 15. Starch | − | − | − |
|   | (No gas production in each case) | | | |
| d) | Other properties | | | |
|   | Growth on SS agar medium | + | + | + |
|   | Growth on MacConkey agar medium | + | + | + |
|   | Growth on 6.5% NaCl | + | + | + |
|   | DNase | + | + | + |
|   | Ornithine decarboxylase | + | + | − |
|   | Arginine dehydrolation | − | − | − |
|   | Gelatin liquefaction | + | + | |
|   | G + C content of DNA | 47.1% | 46.9% | 44.0% |
|   | Na$^+$ requirement | | | + |
|   | Quinone type | | | |
|   | Ubiquinone 7 | | + | + |
|   | Ubiquinone 8 | | + | + |
|   | Menaquinone | | + | + |
|   | Methylmenaquinone | | + | + |

On the basis of the above-mentioned taxonomical properties, and according to criteria described in Bergey's Manual of Determinative Bacteriology, Eighth Ed., 1974 (Reference 1); Manual of Clinical Microbiology, Third Ed., 1980 (Reference 2); Bergey's Manual of Systematic Bacteriology Volume 1, 352, 1984 (Reference 3); and Journal of General Microbiology 129, 3057-3074, 1983 (Reference 4), the above-mentioned strains were identified as follows:

Since SCRC-2181, SCRC-2201, SCRC-2271, SCRC-2341, SCRC-2451, SCRC-2642, SCRC-2792, SCRC-2878, SCRC-3011, and SCRC-3022 are gram negative rod bacteria which are aerobic, motile, have a single polar flagellum, and exhibit catalase and oxidase activities, according to References 1 and 2, they belong to the genus Pseudomonas. These references describe *Pseudomonas putrefaciens* as a species of Pseudomonas, and the properties of these strains substantially correspond to those described in the references. Therefore, the above-mentioned ten strains are identified as *Pseudomonas putrefaciens*. Note, although some properties relating to the production of acids and gas from sugars are not identical to those described in the References, since such properties are not important from the taxonomical point of view, and such properties generally vary within the same species, then such differences have no affect on the above-mentioned identification.

Note, according to the reference 4, however, on the basis of the G+C content in their DNAs, *Pseudomonas putrefaciens* is described as *Alteromonas putrefaciens*. This is also referred to in reference 3. More recently, M. T. MacDonell and R. R. Colwell, Systematic and Applied Microbiology 6, 171-182 (1985) proposed a new genus Shewanella on the basis of a ribonucleotide sequence of 5S rRNA, and suggested that it be designated *Shewanella putrefaciens*.

Since SCRC-2871 is a gram negative rod bacterium which is aerobic, motile, has a single polar flagellum, and exhibits catalase and oxidase activities, and moreover, has a G+C content in their DNAs of 47.1%, according to the above-mentioned references 1, 2, 3, and 4, it belongs to the genus Alteromonas. As a strain belonging to Alteromonas, *Alteromonas putrefaciens* is known, and the above-mentioned taxonomical properties of this strain substantially correspond to those described in the above-mentioned references. Therefore, this strain is identified as *Alteromonas putrefaciens*.

Since SCRC-2874 is a gram negative rod bacterium which is aerobic, motile, has a single polar flagellum, and exhibits catalase and oxidase activities, then according to the references 1 and 2, it belongs to *Pseudomonas putrefaciens*. According to the reference 4, however, on the basis of the G+C content in their DNAs, *Pseudomonas putrefaciens* is described as *Alteromonas putrefaciens*. This is also referred to in reference 3. More recently, M. T. MacDonell and R. R. Colwell, Systematic and Applied Microbiology 6, 171-182 (1985) proposed a new genus Shewanella on the basis of a ribonucleotide sequence of 5S rRNA, and suggested that it be designated *Shewanella putrefaciens*. Therefore, taking this into consideration, SCRC-2874 is identified as *Shewanella putrefaciens*.

SCRC-1162 has the following properties: (1) gram negative, (2) motile, (3) non-sporulation and aerobic rod, (4) O-F test negative, (5) catalase and oxidase positive, (6) nitrate reduction positive, (7) hydrogen sulfide formation positive, (8) gelatin liquefaction and DNA hydrolysis positive, (9) acid formation (+) and gas formation (−) from glucose, (10) quinone type: ubiquinones 7 and 8, menaquinone and methylmenaquinone, (11) peritrichous flagella, and (12) Na+ requirement. On the basis of the above-mentioned properties, according to the References 1, 2, 3, and 4, the strain SCRC-1162 is identified as follows: From the properties (1) to (10), the strain could be considered to be an *Alteromonas putrefaciens* related strain, but since it has peritrichous flagella as observed by electron microscope, does not have an ornithine decarboxylase activity, and requires Na+, the present inventor decided that this strain should belong to a new subspecies, and designated and identified it as *Alteromonas putrefaciens* subspecies sagamifaciens.

The above-mentioned microorganisms were deposited with the Fermentation Research Institute Agency of Industrial Science and Technology, Ministry of International Trade and Industry, 1-1-3 Yatabe-machi Higashi, Tsukuba-shi, Ibaraki-ken, Japan under FERM P-Numbers, and transferred to international deposition under the Deposit of Microorganisms for the Purposes of Patent Procedure (Budapest Treaty) under FERM BP-Numbers as follows:

| | |
|---|---|
| *Pseudomonas putrefaciens* | SCRC-2878 |
| December 26, 1986 | FERM P-9114 |
| December 17, 1987 | FERM BP-1623 |
| *Alteromonas putrefaciens* | SCRC-2871 |
| January 28, 1987 | FERM P-9158 |
| December 17, 1987 | FERM BP-1624 |
| *Shewanella putrefaciens* | SCRC-2874 |
| January 28, 1987 | FERM P-9159 |
| December 17, 1987 | FERM BP-1625 |
| *Alteromonas putrefaciens* subspecies *sagamifaciens* | SCRC-1162 |
| February 20, 1987 | FERM P-9210 |
| December 17, 1987 | FERM BP-1626 |

The above-mentioned strains for the present invention may be converted to strains having an eicosapentaenoic acid productivity higher than the original strain, by conventional mutation and selection procedures.

The microorganisms used in the present invention can be preserved by a conventional method, such as on an agar slant medium or by lyophilization. As the agar slant medium, a conventional medium for the preservation of microorganism belonging the genera Pseudomonas, Alteromonas or Shewanella, for example, the above-mentioned medium, can be used. Lyophilization also may be carried out by a conventional method.

For the production of eicosapentaenoic acid, one of the above-mentioned microorganism is cultured in a medium. The medium may be any medium in which the microorganism used can grow and produce eicosapentaenoic acid. The medium contains, as a nitrogen source, for example, yeast extract, peptone or meat extract, or a combination thereof. Moreover, the medium may contain, as a carbon source, various kinds of sugar such as glucose, fructose, maltose, and sucrose; organic acids, such as intermediates of the TCA cycle such as citrate, fumarate and pyruvate, other organic acids such as maleate and acetate; and amino acids such as aspartate and glutamate. The medium preferably contains sodium chloride, or sea water or artificial sea water. Note, *Alteromonas hanedai*, and *Alteromonas putrefaciens* subspecies sagamifaciens require sodium chloride.

The microorganisms of the present invention can be cultured in a liquid medium or on a solid medium. The pH value of the medium is 6 to 9, preferably 7 to 8. To obtain a large amount of the target product eicosapentaenoic acid, the microorganism is cultured in a liquid medium by stationary culture, or more preferably, by a shaking culture or aeration-agitation culture, under aerobic conditions. The microorganism is cultured at any temperature at which the microorganism can grow and produce eicosapentaenoic acid. The temperature is preferably 5° C. to 30° C., and more preferably, 15° C. to 25° C. For *Alteromonas hanedai*, the temperature is preferably 5° C. to 25° C., and more preferably, 10° C. to 20° C. Culturing is carried out for a period sufficient to produce eicosapentaenoic acid in an amount enough to enable the recovery thereof, preferably for 8 to 48 hours.

Next, eicosapentaenoic acid is recovered from the culture by a conventional procedure used for the isolation and purification of a fatty acid from a culture. For example, the culture is centrifuged or filtered to obtain microbial cells, which are then optionally washed with water, saline or a buffer such as a phosphate buffer. The cells are then resuspended in such a liquid to prepare a cell suspension. Next, the suspension is extracted with a conventional solvent, for example, a mixture of methanol and chloroform. The chloroform phase is then separated and evaporated to obtain a lipid material containing eicosapentaenoic acid. The lipid is then saponified to obtain free eicosapentaenoic acid or a salt thereof.

According to the present invention, a large amount of pure eicosapentaenoic acid and a lipid containing eicosapentaenoic acid can be easily produced in a short time by fermentation.

EXAMPLES

The present invention will now be further illustrated by, but is by no means limited to, the following examples.

Example 1

Production of eicosapentaenoic acid and lipid containing same by *Pseudomonas putrefaciens* SCRC-2878

First, 20 l of a medium containing 1.0% of meat extract, 1.0% of peptone and 0.5% of NaCl (pH 7.0) was filled in a jar fermenter, and after sterilization at 121° C. for 15 minutes, an inoculum of *Pseudomonas putrefaciens* SCRC-2878 (FERM BP-1623) was inoculated to the medium. Culturing was carried out at 25° C. at pH 6.8 to 7.2 for 24 hours under an aerobic condition by aeration and agitation. After the culturing, the culture was centrifuged for 20 minutes at 6000×G to obtain about 150 g of wet cells (corresponding to 16.5 g of dry cells). The cells were washed with 0.85% saline and resuspended in 1 l of the same saline. The suspension was extracted with 1 l of a mixture of chloroform and methanol (2:1 v/v), and the whole was centrifuged to obtain a chloroform phase. To the residual aqueous phase containing cells was added 600 ml of chloroform, and the whole was thoroughly shaken and centrifuged to obtain a chloroform phase. The chloroform phases were combined, and the combined chloroform phase was concentrated to dryness to obtain 1.16 g of a lipid fraction (corresponding to 7.03 g/100 g dry cells). The lipid fraction contained eicosapentaenoic acid. The lipid was saponified in 95% ethanol containing 0.3N NaOH at 80° C. for one hour, to obtain a saponification product containing sodium eicosapentaenoate. The product was then neutralized with 6N HCl to obtain a product containing free eicosapentaenoic acid. Next, the neutralized product was treated with diazomethane to convert free eicosapentaenoic acid to a methyl ester thereof, and the methyl ester-containing product was analyzed by gas chromatography. As a result, it was found to contain 0.114 g (9.8 g/100 g lipid fraction, and 0.69 g/100 g dry cells) of eicosapentaenoic acid.

Example 2

Production of eicosapentaenoic acid and lipid containing same by *Alteromonas putrefaciens* SCRC-2871

First, 20 l of a medium containing 1.0% of meat extract, 1.0% of peptone and 0.5% of NaCl (pH 7.0) was filled in a jar fermenter, and after sterilization at 121° C. for 15 minutes, an inoculum of *Alteromonas putrefaciens* SCRC-2871 (FERM BP-1624) was inoculated to the medium. Culturing was carried out at 25° C. at pH 6.8 to 7.2 for 24 hours under an aerobic condition by aeration and agitation. After the culturing, the cultured broth was centrifuged for 20 minutes at 6,000×G to obtain about 135 g of wet cells (corresponding to 15.0 g of dry cells). The cells were washed with 0.85% saline and resuspended in 1 l of the same saline. The suspension was extracted with 1 l of a mixture of chloroform and methanol (2:1 v/v), and the whole was centrifuged to obtain a chloroform phase. To the residual aqueous phase containing cells was added 600 ml of chloroform, and the whole was thoroughly shaken and centrifuged to obtain the chloroform phase. The chloroform phases were combined, and the combined chloroform phase was concentrated to dryness to obtain 1.05 g of lipid fraction (corresponding to 7.00 g/100 g dry cells). The lipid fraction contained eicosapentaenoic acid. The lipid was saponified in 95% ethanol containing 0.3N NaOH at 80° C. for one hour to obtain a saponification product containing sodium eicosapentaenoate. The product was then neutralized with 6N HCl to obtain a product containing free eicosapentaenoic acid. Next, the neutralized product was treated with diazomethane to convert free eicosapentaenoic acid to a methyl ester thereof, and the methyl ester-containing product was analyzed by gas chromatography. As a result, it was found to contain 0.111 g (10.6 g/100 g lipid fraction, 0.74 g/100 g dry cells) of eicosapentaenoic acid.

The above-mentioned free eicosapentaenoic acid containing product was subjected to silica gel column chromatography using n-hexane/ethyl ether (9:1) as an eluate to obtain a fraction containing purified eicosapentaenoic acid, which fraction was evaporated to dryness to obtain 0.10 g of eicosapentaenoic acid.

Example 3

Production of eicosapentaenoic acid and lipid containing same by *Shewanella putrefaciens* SCRC-2874

First, 20 l of a medium containing 1.0% of meat extract, 1.0% of peptone and 0.5% of NaCl (pH 7.0) was filled in a jar fermenter, and after sterilization at 121° C. for 15 minutes, an inoculum of *Shewanella putrefaciens* SCRC-2874 (FERM BP-1625) was inoculated to the medium. Culturing was carried out at 25° C. at pH 6.8 to 7.2 for 24 hours under an aerobic condition by aeration and agitation. After the culturing, the culture was centrifuged for 20 minutes at 6000×G to obtain about 200 g of wet cells (corresponding to 22.5 g of dry cells). The cells were washed with 0.85% saline, and resuspended in 1 l of the same saline. The suspension was extracted with 1 l of a mixture of chloroform and methanol (2:1 v/v), and the whole was centrifuged to obtain a chloroform phase. To the residual aqueous phase containing cells was added 600 ml of chloroform, and the whole was thoroughly shaken and centrifuged to obtain a chloroform phase. The chloroform phases were combined, and the combined chloroform phase was concentrated to dryness to obtain 1.78 g of lipid fraction (corresponding to 7.91 g/100 g dry cells). The lipid fraction contained eicosapentaenoic acid. The lipid was saponified in 95% ethanol containing 0.3N NaOH at 80° C. for one hour to obtain a saponification product containing sodium eicosapentaenoate. The product was then neutralized with 6N HCl to obtain a product containing free eicosapentaenoic acid. Next, the neutralized product was treated with diazomethane to convert free eicosapentaenoic acid to the methyl ester thereof, and the methyl ester-containing product was analyzed by gas chromatography. As a result, it was found to contain 0.241 g (13.5 g/100 g lipid fraction, 1.07 g/100 g dry cells) of eicosapentaenoic acid.

The above-mentioned free eicosapentaenoic acid containing product was subjected to silica gel column chromatography using n-hexane/ethyl ether (9:1) as an eluate to obtain a fraction containing purified eicosapentaenoic acid, which fraction was evaporated to dryness to obtain 0.22 g of eicosapentaenoic acid.

Example 4

Production of eicosapentaenoic acid and lipid containing same by *Alteromonas putrefaciens* subspecies sagamifaciens SCRC-1162

First, 30 l of a medium containing 1.0% of meat extract, 1.0% of peptone and 0.5% of NaCl (pH 7.0) was filled in a jar fermenter, and after sterilization at 121° C. for 15 minutes, an inoculum of *Alteromonas putrefaciens* subspecies sagamifaciens SCRC-1162 (FERM BP-1626) was inoculated to the medium. Culturing was carried out at 25° C. at pH 6.8 to 7.2 for 24 hours under an aerobic condition by aeration and agitation. After the culturing, the culture was centrifuged for 20 minutes at 6000×G to obtain about 205 g of wet cells (corresponding to 25.6 g of dry cells). The cells were washed with 0.85% saline, and resuspended in 1.5 l of the same saline. The suspension was extracted with 1.5 l of a mixture of chloroform and methanol (2:1 v/v), and the whole was centrifuged to obtain a chloroform phase. To the residual aqueous phase containing cells was added 900 ml of chloroform, and the whole was thoroughly shaken and centrifuged to obtain a chloroform phase. The chloroform phases were combined, and the combined chloroform phase was concentrated to dryness to obtain 2.13 g of lipid fraction (corresponding to 8.32 g/100 g dry cells). The lipid fraction contained eicosapentaenoic acid. The lipid was saponified in 95% ethanol containing 0.3N NaOH at 80° C. for one hour to obtain a saponification product containing sodium eicosapentaenoate. The product was then neutralized with 6N HCl to obtain a product containing free eicosapentaenoic acid. Next, the neutralized product was treated with diazomethane to convert free eicosapentaenoic acid to the methyl ester thereof, and the methyl ester-containing product was analyzed by gas chromatography. As a result, it was found to contain 0.205 g (9.6 g/100 g lipid fraction, 0.80 g/100 g dry cells) of eicosapentaenoic acid.

The above-mentioned free eicosapentaenoic acid containing product was subjected to reverse phase silica gel column chromatography using methanol as an eluate to obtain a fraction containing purified eicosapentaenoic acid, which fraction was evaporated to dryness to obtain 0.185 g of eicosapentaenoic acid.

Example 5

Production of eicosapentaenoic acid and lipid containing same by *Alteromonas hanedai* IAM-12641

First, 20 l of a medium containing 1.0% of meat extract, 1.0% of peptone and 0.5% of NaCl (pH 7.0) was filled in a jar fermenter, and after sterilization at 121° C. for 15 minutes, an inoculum of *Alteromonas hanedai* IAM-12641 was inoculated to the medium. Culturing was carried out at 15° C. at pH 6.8 to 7.2 for 24 hours under an aerobic condition by aeration and agitation. After the culturing, the culture was centrifuged for 20 minutes at 6000×G to obtain about 150 g of wet cells (corresponding to 14.9 g of dry cells). The cells were washed with 0.85% saline, and resuspended in 1 l of the same saline. The suspension was extracted with 1 l of a mixture of chloroform and methanol (2:1 v/v), and the whole was centrifuged to obtain a chloroform phase. To the residual aqueous phase containing cells was added 600 ml of chloroform, and the whole was thoroughly shaken and centrifuged to obtain a chloroform phase. The chloroform phases were combined, and the combined chloroform phase was concentrated to dryness to obtain 1.18 g of lipid fraction (corresponding to 7.92 g/100 g dry cells). The lipid fraction contained eicosapentaenoic acid. The lipid was saponified in 95% ethanol containing 0.3N NaOH at 80° C. for one hour to obtain a saponification product containing sodium eicosapentaenoate. The product was then neutralized with 6N HCl to obtain a product containing free eicosapentaenoic acid. Next, the neutralized product was treated with diazomethane to convert free eicosapentaenoic acid to the methyl ester thereof, and the methyl ester-containing product was analyzed by gas chromatography. As a result, it was found to contain 0.145 g (12.3 g/100 g lipid fraction, 0.97 g/100 g dry cells) of eicosapentaenoic acid.

The above-mentioned free eicosapentaenoic acid containing product was subjected to reverse phase silica gel column chromatography using methanol as an eluate to obtain a fraction containing purified eicosapentaenoic acid, which fraction was evaporated to dryness to obtain 0.126 g of eicosapentaenoic acid.

We claim:

1. A process for producing eicosapentaenoic acid comprising the steps of:

(a) culturing a microorganism selected from the group consisting of *Pseudomonas putrefaciens* SCRC-2181, SCRC-2201, SCRC-2271, SCRC-2341, SCRC-2451, SCRC-2642, SCRC-2792, SCRC-2878, SCRC-3011, SCRC-3022, and a *Pseudomonas putrefaciens* strain having all of the identifying characteristics of any one of said strains in an aqueous nutrient medium containing assimilable sources of carbon, nitrogen and inorganic substances, to produce a lipid containing eicosapentaenoic acid; and (b) recovering the eicosapentaenoic acid from the cultured product.

2. A process for producing a lipid containing eicosapentaenoic acid comprising the steps of:

(a) culturing a microorganism selected from the group consisting of *Pseudomonas putrefaciens* SCRC-2181, SCRC-2201, SCRC-2271, SCRC-2341, SCRC-2451, SCRC-2642, SCRC-2792, SCRC-2878, SCRC-3011, SCRC-3022, and a *Pseudomonas putrefaciens* strain having all of the identifying characteristics of any one of said strains in an aqueous nutrient medium containing assimilable sources of carbon, nitrogen and inorganic substances, to produce a lipid containing eicosapentaenoic acid; and (b) recovering the lipid from the cultured product.

3. A process for producing eicosapentaenoic acid comprising the steps of:

(a) culturing a microorganism selected from the group consisting of *Shewanella putrefaciens* SCRC-2874, and a *Shewanella putrefaciens* strain having all of the identifying characteristics of said strain in an aqueous nutrient medium containing assimilable sources of carbon, nitrogen and inorganic substances, to produce a lipid containing eicosapentaenoic acid; and (b) recovering the eicosapentaenoic acid from the cultured product.

4. A process for producing a lipid containing eicosapentaenoic acid comprising the steps of:
  (a) culturing a microorganism selected from the group consisting of *Shewanella putrefaciens* SCRC-2874, and a *Shewanella putrefaciens* strain having all of the identifying characteristics of said strain in an aqueous nutrient medium containing assimilable sources of carbon, nitrogen and inorganic substances, to produce a lipid containing eicosapentaenoic acid; and
  (b) recovering the lipid from the cultured product.

5. A process for producing eicosapentaenoic acid comprising the steps of:
  (a) culturing a microorganism selected from the group consisting of *Alteromonas putrefaciens* subspecies sagamifaciens SCRC-1162, *Alteromonas putrefaciens* SCRC-2871, and an *Alteromonas putrefaciens* strain having all of the identifying characteristics of any one of said strains in an aqueous nutrient medium containing assimilable sources of carbon, nitrogen and inorganic substances, to produce a lipid containing eicosapentaenoic acid; and
  (b) recovering the eicosapentaenoic acid from the cultured product.

6. A process for producing a lipid containing eicosapentaenoic acid comprising the steps of:
  (a) culturing a microorganism selected from the group consisting of *Alteromonas putrefaciens* subspecies sagamifaciens SCRC-1162, *Alteromonas putrefaciens* SCRC-2871, and an *Alteromonas putrefaciens* strain having all of the identifying characteristics of any one of said strains, to produce a lipid containing eicosapentaenoic acid; and
  (b) recovering the lipid from the cultured product.

7. A biologically pure culture of a microorganism capable of producing eicosapentaenoic acid selected from the group consisting of *Pseudomonas putrefaciens* SCRC-2181, *Pseudomonas putrefaciens* SCRC-2201, *Pseudomonas putrefaciens* SCRC-2271, *Pseudomonas putrefaciens* SCRC-2341, *Pseudomonas putrefaciens* SCRC-2451, *Pseudomonas putrefaciens* SCRC-2642, *Pseudomonas putrefaciens* SCRC-2792, *Pseudomonas putrefaciens* SCRC-2878, *Pseudomonas putrefaciens* SCRC-3011, *Pseudomonas putrefaciens* SCRC-3022, *Alteromonas putrefaciens* subspecies sagamifaciens SCRC-1162, *Alteromonas putrefaciens* SCRC-2871, and *Shewanella putrefaciens* SCRC-2874.

* * * * *